United States Patent
Saint-Leger

(10) Patent No.: US 6,759,051 B2
(45) Date of Patent: Jul. 6, 2004

(54) COSMETIC OR DERMATOLOGICAL COMPOSITION COMPRISING AT LEAST ONE ALKYNYL CARBAMATE AND AT LEAST ONE POLYOL

(75) Inventor: Didier Saint-Leger, Courbevoie (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/449,924

(22) Filed: Dec. 2, 1999

(65) Prior Publication Data

US 2001/0051169 A1 Dec. 13, 2001

(30) Foreign Application Priority Data

Dec. 3, 1998 (FR) .............................. 98 15304

(51) Int. Cl.[7] .............................. A61K 7/00; A61K 9/00; A61K 7/06; A01N 25/00
(52) U.S. Cl. ...................... 424/401; 424/47; 424/70.1; 424/70.8; 424/400; 424/405
(58) Field of Search ................. 424/401, 70.1, 424/70.8, 400, 405, 44

(56) References Cited

U.S. PATENT DOCUMENTS

| | | | | |
|---|---|---|---|---|
| 5,552,425 A | * | 9/1996 | Merianos | 514/390 |
| 5,833,742 A | * | 11/1998 | Willingham et al. | 106/18.32 |
| 5,965,594 A | * | 10/1999 | Schoenberg et al. | 514/389 |
| 5,968,528 A | * | 10/1999 | Deckner et al. | 424/401 |

FOREIGN PATENT DOCUMENTS

| | | |
|---|---|---|
| EP | 0 705 595 A2 | 4/1996 |
| EP | 0819427 | 1/1998 |
| FR | 2 751 217 | 1/1998 |
| FR | 2 758 722 | 7/1998 |
| WO | 95/29588 | 11/1995 |
| WO | WO 95/29588 | 11/1995 |
| WO | WO 96/24329 | 8/1996 |
| WO | WO 99 49730 | 10/1999 |

OTHER PUBLICATIONS

DEKABEN LMB (IPBC) Product Data Sheet (Aug. 11, 1997) (2 pages).
Glycacil –S Product Data Sheet (Aug. 31, 1993) (5 pages).

* cited by examiner

*Primary Examiner*—Barbara P. Badio
*Assistant Examiner*—Marina Lamm
(74) *Attorney, Agent, or Firm*—Nixon & Vanderhye P.C.

(57) ABSTRACT

The present invention consists of a cosmetic or dermatological composition comprising, in a physiologically acceptable medium:

at least one alkynyl carbamate of formula (I) below:

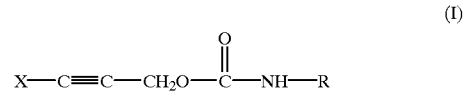

(I)

in which:

A denotes a halogen atom

R denotes a hydrogen atom,
an alkyl group,
a hydroxyalkyl group, and at least one polyol chosen from non-etherified polyols, and (poly)alkyl or (poly)alkenyl polyol ethers; these polyols containing from 4 to 28 carbon atoms and from 2 to 6 hydroxyl functions, with the proviso that at least two of these hydroxyl functions are free;

uses of these compositions and a cosmetic treatment process using these compositions.

16 Claims, No Drawings

COSMETIC OR DERMATOLOGICAL COMPOSITION COMPRISING AT LEAST ONE ALKYNYL CARBAMATE AND AT LEAST ONE POLYOL

The present invention relates to cosmetic or dermatological compositions comprising at least one alkynyl carbamate and at least one polyol; to the use of these compositions in cosmetics; and to the use, for the preparation of a cosmetic or dermatological composition, of an alkynyl carbamate and a polyol for treating inflammatory and/or desquamating skin disorders associated with Malassezia spp.

Desquamating disorders of the scalp such as dandruff and seborrhoeic dermatitis are associated with the presence of a characteristic yeast known as Malassezia ovalis, which was previously known as Pityrosporum (P. ovale and P. orbiculare).

Moreover, it is known that this yeast is capable of changing its shape and metabolism. In particular, it can change into a filamentous form (Malassezia furfur) which is responsible for the inflammatory and pigmentary disorder known as Pityriasis versicolor.

The usual treatment for all these complaints involves using antifungal agents in a medium, such as a shampoo, a gel or a lotion, which is suitable for distributing these agents and depositing them on teguments.

The antifungal activity of these agents is limited; furthermore, the persistence of the antifungal activity is low. Thus, treatments using these antifungal agents are of very moderate or even low efficacy.

The Applicant has thus sought to solve these problems and to obtain more effective treatments.

It has discovered, surprisingly, that by combining an alkynyl carbamate with certain polyols, it is possible to obtain treatments that are much more effective than those of the prior art. Specifically, the Applicant has discovered, surprisingly, that these combinations have strong and long-lasting antifungal activity directed against Malassezia spp.

It has been noted in particular that combinations of these compounds as doses at which each of their individual activities is lost, remain effective and have reinforced antifungal activity.

It has also been found that the combinations of the invention have good solubility and stability in the media usually used for applying antifungal compositions, as well as good skin tolerance.

A subject of the present invention is thus a cosmetic or dermatological composition comprising, in a physiologically acceptable medium, at least one alkynyl carbamate and at least one polyol.

Another subject of the invention relates to the use of these compositions as antifungal or antidandruff cosmetic compositions.

Another subject of the invention is also the use of an alkynyl carbamate and a polyol to prepare an antidandruff or antifungal dermatological composition.

Another subject of the invention consists of a cosmetic treatment process for eliminating dandruff from the hair and the scalp using these compositions.

Other subjects of the invention will become apparent in the light of the description and the examples which follow.

A subject of the present invention is essentially a cosmetic or dermatological composition, characterized in that it comprises, in a physiologically acceptable medium: at least one alkynyl carbamate of formula (I) below:

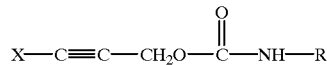

(I)

in which:
X denotes a halogen atom
R denotes a hydrogen atom,
an alkyl group,
a hydroxyalkyl group,
and at least one polyol chosen from non-etherified polyols, $C_1$–$C_{10}$ (poly)alkyl or $C_2$–$C_{20}$ (poly)alkenyl polyol ethers and glycosyl polyol ethers; the polyol being saturated or unsaturated, linear, branched or cyclic, bearing or not bearing a hetero atom, and bearing or not bearing additional chemical functions chosen from carbonyl and carboxyl functions.

In the context of the present invention:
the term "halogen atom" denotes a fluorine, chlorine, bromine or iodine atom and preferably an iodine atom.
The term "alkyl group" denotes linear or branched groups containing from 1 to 20 carbon atoms, such as, for example, octyl, nonyl, decyl, dodecyl or pentadecyl groups. The term "alkyl group" preferably denotes lower alkyl groups containing from 1 to 4 carbon atoms in a linear or branched chain, such as, for example, methyl, ethyl, propyl, isopropyl, n-propyl, butyl, n-butyl or tert-butyl groups.

The compositions of the invention preferably contain compounds of formula (I) in which X denotes an iodine atom and R denotes a lower alkyl group containing from 1 to 4 carbon atoms.

Even more preferably, they contain at least 3-iodo-2-propynyl butylcarbamate.

According to the invention, the polyols represent saturated or unsaturated, linear, branched or cyclic compounds bearing or not bearing a hetero atom, and bearing or not bearing additional chemical functions chosen from carbonyl and carboxyl functions.

Among these compounds, mention may be made of erythritol, arabitol, adonitol, sorbitol, dulcitol, 1,2-butanediol, 1,3-butanediol, 1,4-butanediol, 2,3-butanediol, 1,5-pentanediol, 2,4-pentanediol, 2-methyl-2,4-pentanediol, 1,6-hexanediol, 2,3-dimethyl-2,3-butanediol, 2,2-diethyl-1, 3-propanediol, 2-ethyl-1,3-hexanediol, 2,2,4-trimethyl-1,3-pentanediol, 2-ethyl-2-butyl-1,3-propanediol, 1,2,4-butanetriol, 1,2,6-hexanetriol, 2,2-dihydroxymethyl-1-butanol, tetramethylolmethane (pentaerythritol), glyceryl α-monomethyl ether, glyceryl α-mono-n-butyl ether and 2-O-α-D-glucopyranosyl-L-ascorbic acid.

The polyol preferably used is 3-(2-ethyl-hexyloxy)-1,2-propanediol ($C_{11}H_{24}O_3$).

The alkynyl carbamate and the polyol can be simultaneously present in individual proportions or between 0.001% and 10% by weight relative to the total weight of the composition and preferably in proportions of between 0.01% and 5% by weight relative to the total weight of the composition.

The weight ratio of the alkynyl carbamate and of the polyol can range from 0.01 to 100 and preferably from 0.05 to 5.

The compositions of the invention can have a pH of between 2 and 12.

The physiologically acceptable medium generally consists of water or of mixture of water and at least one organic solvent which is physiologically acceptable for the purpose of topical application. Among the solvents which may be mentioned are $C_1$–$C_4$ lower alcohols such as ethanol, isopropyl alcohol, alkylene glycols such as propylene glycol, ethylene glycol monobutyl ether, and propylene glycol and dipropylene glycol mono(or di)ethyl(or methyl) ether. When they are present, these solvents preferably represent from 1 to 80% by weight relative to the total weight of the composition.

The compositions according to the invention can be in the form of lotions, shampoos, mousses, creams, gels, sticks, sprays, balms, powders or solid or liquid soaps.

The compositions in accordance with the invention can optionally also contain various additives other than those defined above, which do not adversely affect the properties of the compositions of the invention, such as anionic, amphoteric, zwitterionic or nonionic surfactants, suspending agents, anionic, nonionic, cationic or amphoteric polymers, proteins, silicone oils, waxes, resins and/or gums, acidifying or basifying agents, preserving agents, fragrances or other adjuvants commonly used in cosmetics or dermatology.

The compositions according to the invention can also contain other antibacterial agents such as those described above, for instance chloramine T, Irgasan DP 300, chloramine B, 1,3-dibromo-5,5-dimethylhydantoin, 1,3-dichloro-5,5-dimethylhydantoin, 3-bromo-1-chloro-5,5-dimethylhydantoin or N-chlorosuccinimide.

They can also contain antifungal agents such as, for example, selenium sulphide, zinc pyrindinethione or octopyrox.

A subject of the invention is thus the use of a composition as defined above for the cosmetic treatment of the hair and the scalp.

A subject of the invention is also the use of a composition as defined above, as an antifungal cosmetic composition.

More particularly, the compositions of the invention are preferably used as antidandruff cosmetic compositions.

The invention also relates to the use of alkynyl carbamate as defined above and of at least one polyol as defined above for the preparation of an antifungal dermatological composition or for the preparation of a dermatological composition intended for the treatment of inflammatory and/or desquamating skin disorders associated with Malassezia spp. and more particularly antidandruff treatment.

A subject of the present invention is also a cosmetic treatment process in which the cosmetic compositions according to the invention are used to eliminate dandruff from the hair and the scalp, and they are applied, in this case, to wet or dry hair; these applications optionally being followed by a rinsing operation.

In one preferred embodiment of the invention, the compositions according to the invention are used as shampoos for washing and treating the hair and the scalp.

In this case, they are applied to wet or dry hair in amounts which are effective for washing them, this application being followed by a rinsing operation.

The examples which follow illustrate the present invention without, however, being limiting in nature.

In the examples which follow, the following definitions apply:
Compound A: 3-iodo-2-propynyl butyl carbamate, and
Compound B: 3-(2-ethylhexyloxy)-1,2-propanediol

EXAMPLE I

Antidandruff Lotion

| Compound A | 0.1 g AM |
| Compound B | 0.2 g |
| 95° ethanol | 30 g |
| Water | qs 100 g |

This solution is applied daily at a rate of 6 ml to the scalp for 1 to 2 weeks. A considerable improvement in the state of the dandruff is thus observed.

EXAMPLE II

Antidandruff Shampoo

| Compound A | 0.1 g AM |
| Compound B | 1.0 g |
| Sodium lauryl ether sulphate (2.2 EO) | 14 g AM |
| Cocylbetaine | 2.4 g AM |
| Water | qs 100 g |

This shampoo is used daily at a rate of 10 g per scalp with an exposure time of about one minute, and for a period of 2 weeks. A marked improvement in the state of the dandruff is thus observed.

EXAMPLE III

Antidandruff Shampoo

| Compound A | 0.1 g AM |
| Compound B | 1.0 g |
| Sodium lauryl ether sulphate (2.2 EO) | 8 g AM |
| $C_8$/$C_{10}$/$C_{12}$/$C_{14}$ alkyl polyglycoside (1, 4) | 6 g AM |
| Water | qs 100 g |

This shampoo is used daily at a rate of 10 g per scalp with an exposure time of about one minute, and for a period of 2 weeks. A marked improvement in the state of the dandruff is thus observed.

EXAMPLE IV

Determination of the Antifungal Activity of the Combination of Compounds (A) and (B)

The activity of the combination of compound (A) and compound (B) was determined by a conventional method known as the MIC (Minimum Inhibitory Concentration), the MIC corresponding to the concentration at which a given protein inhibits the growth of a given strain under defined conditions.

In this instance, strains of Pityrosporum ovale from the Institut Pasteur, reference CIP 1363.82, were used.

An inoculum of a fresh culture, of 1 to $10 \times 10^7$ cells/ml, is introduced into a Sabouraud+Tween 40 at 10 g/l+glyceryl monooleate at 2.5 g/l agar medium, in the presence or absence of the compound or of the combination of the compounds to be studied, and incubated for 48 hours at 30° C.

The concentration of the compound or combination of compounds above which the growth of the microorganism is completely inhibited (absence of cloudiness of the medium) is thus determined.

For compound (A) by itself and compound (B) by itself, not combined together, at the concentration MIC/2, the growth is identical to that of the control medium, i.e. the medium without any antibacterial compound.

On the other hand, the growth is blocked by the combination of compound (A) at MIC/2+compound (B) at MIC/2.

These results thus show that this combination of compounds, at doses at which each of their individual activities is lost, remains effective and shows reinforced antifungal activity.

What is claimed is:

1. Cosmetic or dermatological composition consisting essentially of, in a physiologically acceptable medium:
   (a) 3-iodo-2-propynyl butylcarbamate, and
   (b) 3-(2-ethylhexyloxy)-1,2-propanediol.

2. Composition according to claim 1, further containing an antibacterial agent selected from the group consisting of chloramine T, Irgasan DP 300, chloramine B, 1,3-dibromo-5,5-dimethylhydantoin, 1,3-dichloro-5,5-dimethylhydantoin, 3-bromo-1-chloro-5,5-dimethylhydantoin and N-chlorosuccinimide.

3. Composition according to claim 1, wherein the component (a) and the component (b) are simultaneously present in individual proportions of between 0.001% and 10% by weight relative to the total weight of the composition.

4. Composition according to claim 1, wherein the component (a) and the component (b) are simultaneously present in individual proportions of between 0.01% and 5% by weight relative to the total weight of the composition.

5. Composition according to claim 1, wherein the weight ratio of the component (a) to the component (b) ranges from 0.01 to 100.

6. Composition according to claim 1, wherein the weight ratio of the component (a) to the component (b) ranges from 0.05 to 5.

7. Composition according to claim 1, having a pH of between 2 and 12.

8. Composition according to claim 1, wherein the physiologically acceptable medium consists of water or of a mixture of water and at least one organic solvent selected from the group consisting of $C_1$–$C_4$ lower alcohols, alkylene glycol, ethylene glycol monobutyl ether, and propylene glycol and dipropylene glycol mono(or di)ethyl (or methyl) ether, present, in proportions of between 1 and 80% by weight relative to the total weight of the composition.

9. Composition according to claim 1, in the form of lotions, shampoos, mousses, creams, gels, sticks, sprays, balms, powders or solid or liquid soaps.

10. Composition according to claim 1, further comprising at least one additive selected from the group consisting of anionic, amphoteric, zwitterionic or nonionic surfactants, suspending agents, anionic, nonionic, cationic or amphoteric polymers, proteins, silicone oils, waxes, resins and/or gums, acidifying or basifying agents, preserving agents, fragrances, antibacterial agents, antifungal agents or other adjuvants commonly used in cosmetics or dermatology.

11. Cosmetic treatment process for eliminating dandruff from the hair and the scalp, comprising applying a composition of claim 1 to wet or dry hair, and this is optionally followed by a rinsing operation.

12. A cosmetic treatment method of the hair or scalp comprising applying the composition of claim 1 to said hair or scalp.

13. A cosmetic antifungal treatment method comprising applying the composition of claim 1 to the hair or scalp of an individual in need of said treatment.

14. A cosmetic antidandruff cosmetic treatment method comprising applying the composition of claim 1 to the hair or scalp of an individual in need of said treatment.

15. A method of making a dermatological composition for treatment of inflammatory and/or desquamating skin disorders comprising mixing 3-iodo-2-propynyl butylcarbamate and 3-(2-ethylhexyloxy)-1,2-propanediol in a cosmetic composition.

16. A method of treating inflammatory and/or desquamating skin disorders associated with Malassezia spp comprising applying the composition of claim 1 to the skin or scalp of a person in need of said treatment.

* * * * *